United States Patent [19]

Nathan

[11] Patent Number: 5,312,367
[45] Date of Patent: May 17, 1994

[54] NEEDLE COVER ASSEMBLY FOR SYRINGES

[76] Inventor: Rasa N. Nathan, 214 N. Elm Dr., Beverly Hills, Calif. 90210

[21] Appl. No.: 63,946

[22] Filed: May 20, 1993

[51] Int. Cl.⁵ .............................................. A61M 5/32
[52] U.S. Cl. ..................................... 604/192; 604/263
[58] Field of Search ................ 604/192, 187, 110, 263

[56] References Cited

U.S. PATENT DOCUMENTS

| | | | |
|---|---|---|---|
| 4,664,259 | 5/1987 | Landis | 604/263 X |
| 4,820,277 | 4/1989 | Norelli | |
| 4,838,871 | 6/1989 | Luther | |
| 4,886,503 | 12/1989 | Miller | |
| 4,909,792 | 3/1990 | Norelli | |
| 4,944,731 | 7/1990 | Cole | 604/192 |
| 4,950,249 | 8/1990 | Jagger et al. | |
| 4,966,591 | 10/1990 | Yuen | |
| 5,011,475 | 4/1991 | Olson | |
| 5,055,102 | 10/1991 | Sitnik | |

*Primary Examiner*—John D. Yasko
*Attorney, Agent, or Firm*—Thomas I. Rozsa; Tony D. Chen

[57] ABSTRACT

The present invention is a needle cover assembly for a syringe. The present invention relates to a two-part needle cover assembly. One part of the cover extends over the head of the needle so that the split is not symmetrically down the middle of the cover but is instead along an arc greater than 180°. There are two halves to the needle cover assembly but they are not split evenly, they are instead around 270° or so for one part and 90° for the other part. The two halves of needle cover assembly are hingeably attached to a hollow hub. A rotatable collar surrounds the hollow hub, and when the rotatable collar is rotated by 90°, the two halves are apart so that the portions of the needle cover are away from each other, thereby exposing the needle so that it can be used for injecting a person with medicine. After the injection has been given, the two halves of the needle cover assembly can be closed by rotating the rotatable collar 90°.

6 Claims, 2 Drawing Sheets

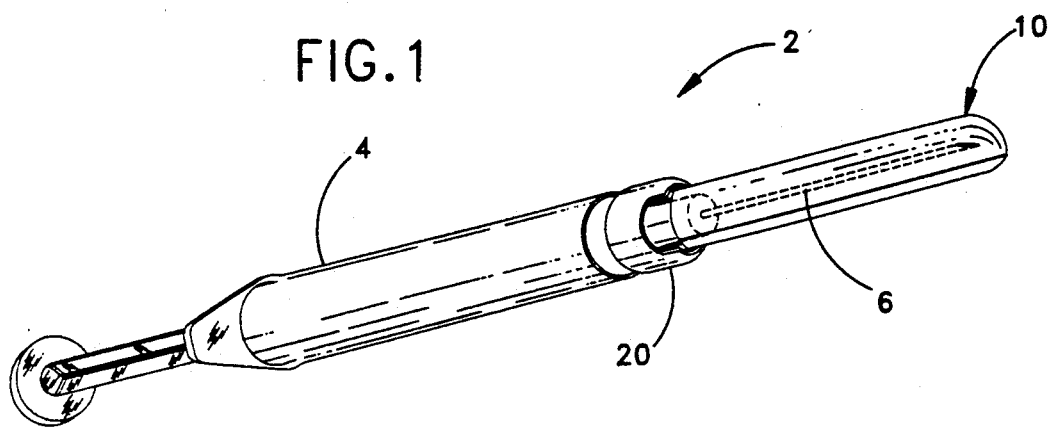
FIG. 1
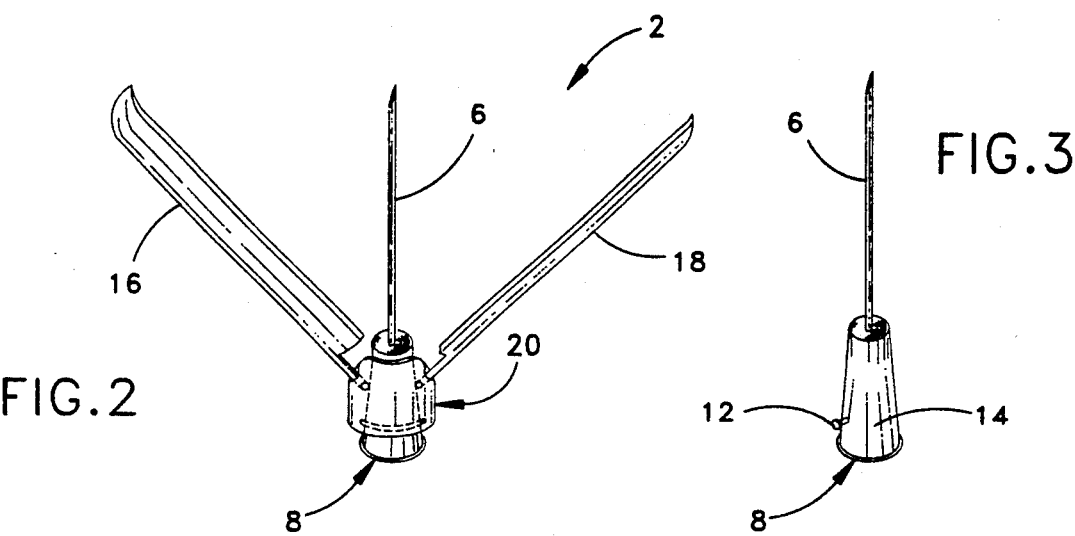
FIG. 2
FIG. 3
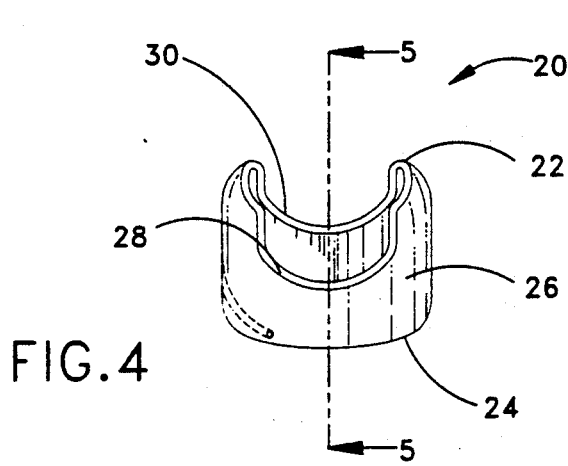
FIG. 4
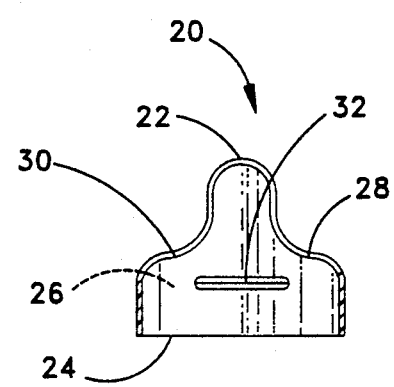
FIG. 5

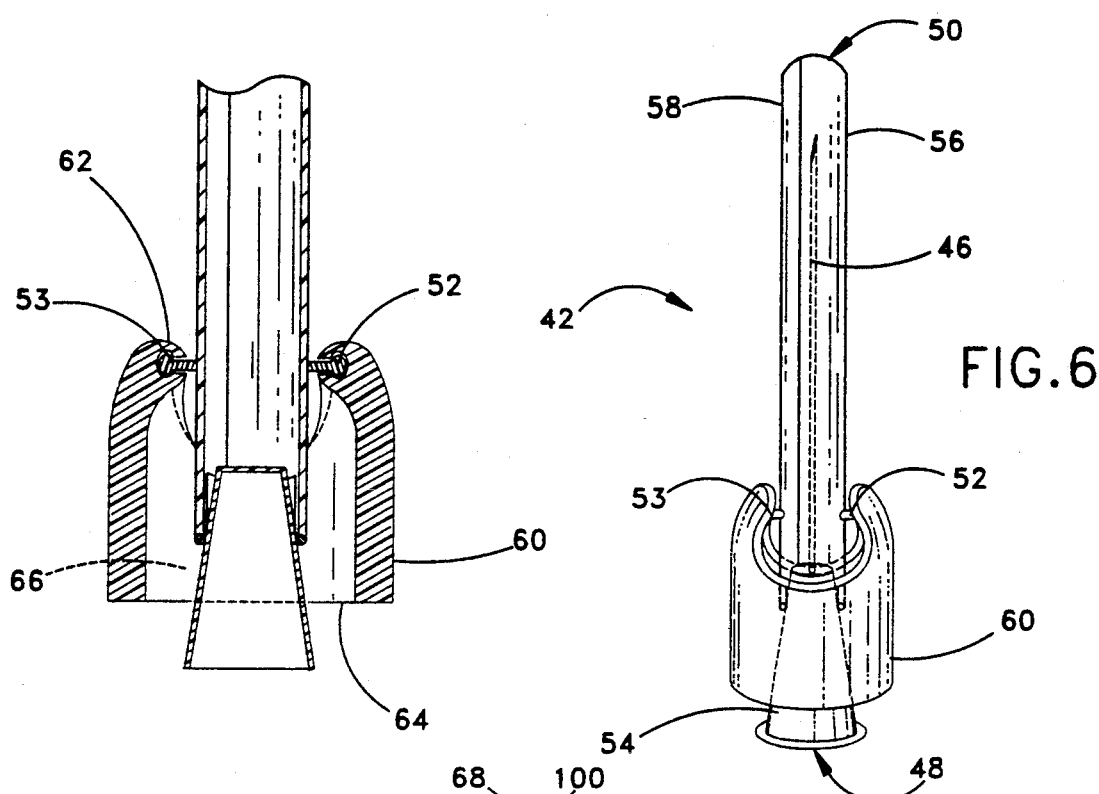
FIG.9
FIG.6
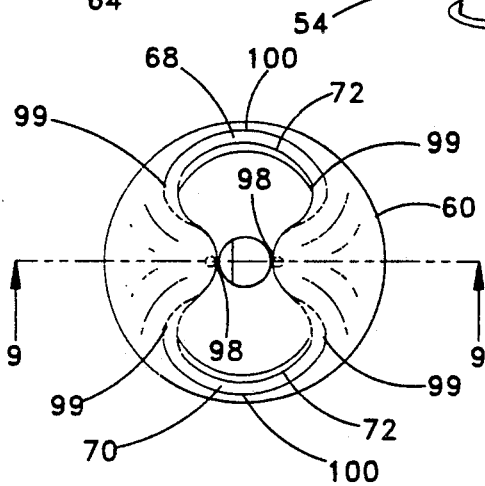
FIG.7
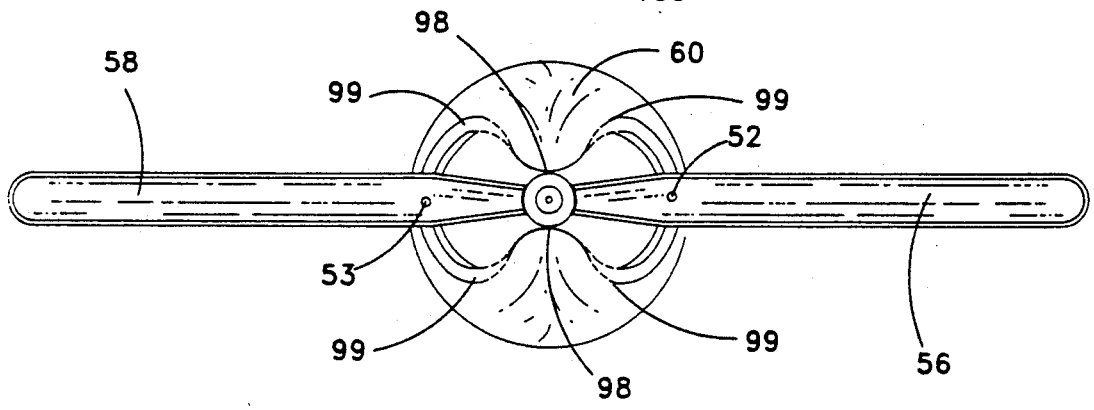
FIG.8

NEEDLE COVER ASSEMBLY FOR SYRINGES

BACKGROUND OF THE INVENTION

1. Field of the Invention

The present invention relates to the field of syringe needles. In particular, the present invention relates to a needle cover assembly for a syringe.

2. Description of the Prior Art

A common problem frequently encountered in hospitals and other medical facilities where injections are given is that when the doctor or nurse recaps the cover back onto the hypodermic needle, there is a motion of the hypodermic needle advancing toward the person's hand holding the cover and sometimes when recapping the cover onto the hypodermic needle, they accidentally prick themselves. This is a serious problem today when the injection has been given to someone with a serious disease such as the well known Acquired Immuno Deficiency Syndrome (AIDS).

The conventional hypodermic needles provide no safe way for recapping the cover onto the hypodermic needle after use and consequently, used hypodermic needles are the most common cause of accidental prick injuries in hospital. This problem has led to the present invention needle cover assembly.

The following prior art references were found relevant to the field of the present invention.

1. U.S. Pat. No. 4,820,277 issued to Norelli on Apr. 11, 1989 for "Safety Cover For Syringe Needles" (hereafter "the Norelli '277 Patent").

2. U.S. Pat. No. 4,838,871 issued to Luther on Jun. 13, 1989 for "Needle Guard, And Assembly" (hereafter "the Luther Patent").

3. U.S. Pat. No. 4,886,503 issued to Miller on Dec. 12, 1989 for "Disposable Covered Needle For Syringe" (hereafter "the Miller Patent").

4. U.S. Pat. No. 4,909,792 issued to Norelli on Mar. 20, 1990 for "Safety Cover For Syringe Needles" (hereafter "the Norelli '792 Patent").

5. U.S. Pat. No. 4,950,249 issued to Jagger et al. on Aug. 21, 1990 for "Hypodermic Needle With Reclosable Safety Cap" (hereafter "the Jagger Patent").

6. U.S. Pat. No. 4,966,591 issued to Yuen on Oct. 30, 1990 for "Needle Assembly" (hereafter "the Yuen Patent").

7. U.S. Pat. No. 5,011,475 issued to Olson on Apr. 30, 1991 for "Protector For Intravenous And Syringe Needles" (hereafter "the Olson Patent").

8. U.S. Pat. No. 5,055,102 issued to Sitnik on Oct. 8, 1991 for "Swing-Away Disposable Syringe Needle Cover" (hereafter "the Sitnik Patent").

The Norelli '277 Patent discloses a safety cover for conventional needle. It includes a pair of elongated semi-cylindrical jaws which cooperate to completely encase a conventional needle. Each jaw is hingeably attached to the syringe barrel. When the jaws are opened, the jaws are generally parallel to each other and adjacent to the syringe. The two jaws are symmetrically split.

The Luther Patent discloses an assembly of a needle guard for a hub and attached needle. It includes an elongated cylindrical guard member mounted on the hub. The cylindrical guard member defines a longitudinal slot which coincides with the needle. The guard member can be rotated away from the needle when in use.

The Miller Patent discloses a disposable covered needle for syringe. It includes a needle member and a cover member pivotably connected to each other. The cover member has a long narrow opening for the needle to pass through when the cover member is pivoted away and is covered by a rupturable plastic film which breaks when the cover is pivoted to expose the needle.

The Norelli '792 Patent discloses a safety cover for syringe needles similar to the Norelli '277 Patent.

The Jagger Patent discloses a hypodermic needle apparatus. The needle cap is split longitudinally into two halves which, in the closed position, abut each other. A ring is used to hold the two halves in the closed position. The ring is threadedly mounted on a threaded portion of the hub which extends upwardly from a base which is used to attach the apparatus to a conventional syringe. The two halves spring outwardly into the perpendicular position when in use. The two halves are symmetrically split and can be rotated to lock and unlock the two halves.

The Sitnik Patent discloses a swing-away disposable syringe needle cover. It includes a tube which is closed on one end and has a longitudinal slit at the other end, which is sufficiently long and wide to permit the needle to traverse through the slit laterally. The tube cover is rotated to the perpendicular position to expose the needle.

The Yuen Patent discloses a needle assembly for withdrawing body fluids. The two cover elements are pivotally connected to the body for rotation toward and away from each other in a plane containing the needle about two pivot points. The two cover elements spring outwardly into the perpendicular position. Each cover element has two halves which are symmetrically split.

The Olson Patent discloses a projector assembly. It includes an elongated hollow protective sheath mounted on the hub and having openings extending longitudinally along both sides thereof to permit the needle to be inserted into one of two conduits. The top of the protective sheath has an opening.

Therefore, the purpose of the present invention is to eliminate the situation where someone has a hypodermic needle which is required to be in motion toward a person's hand when the cover is to be recapped onto the hypodermic needle. In addition, there is a need for an improved needle cover assembly which simplifies the recapping of the cover onto the hypodermic needle.

SUMMARY OF THE INVENTION

The present invention is a needle cover assembly for a syringe. The present invention relates to a two-part needle cover assembly. One part of the cover extends over the head of the needle so that the split is not symmetrically down the middle of the cover but is instead along an arc greater than 180°. Therefore, there are two halves to the needle cover assembly but they are asymmetrical; for example they may be around 270° or so for one part and 90° for the other part.

The two halves of the needle cover assembly are hingeably attached to a hollow hub. A rotatable collar surrounds the hollow hub, and when the rotatable collar is rotated by 90°, the two halves are able to break apart so that the portions of the needle cover are away from each other, thereby exposing the needle so that it can be used for injecting a person with medicine. After the injection has been given, the two halves of the needle cover assembly can be closed by rotating the rotatable collar 90°.

It has been discovered, according to the present invention, that by utilizing a hypodermic needle within the needle cover assembly, it will provide a safe and easy way to install the hypodermic needle onto the syringe without being accidentally pricked by the hypodermic needle.

It has also been discovered, according to the present invention, that if the needle cover assembly is made with a cover comprising two unequal halves, it will provide a way to split the cover to inject the medicine to a patient while at the same time covering the tip of the needle when it is not in use.

It has additionally been discovered, according to the present invention, that if the needle cover assembly is made with a rotatable collar, it will provide a way to open and close the cover.

It has further been discovered, according to the present invention, that if the collar of needle cover assembly has a locking groove in the interior surface of the collar, it will provide a unique way of rotating the collar to open or closed the cover on the needle cover assembly.

It has also been discovered, according to the present invention, that in prior art covers where the two halves are equal, they come together in line with the tip of the needle and a crack at their area of joinder permits a user to accidentally prick himself even when the cover is close. It has been discovered that by making the halves uneven such that the large half covers the needle in the closed position, this problem is eliminated.

It is therefore an object of the present invention to provide an improved needle cover assembly for a syringe.

It is an additional object of the present invention to provide a needle cover assembly which is simple in design and inexpensive to manufacture and which can be safe and easy to use.

It is a further object of the present invention to provide a needle cover assembly which can be connected to a syringe by pushfit or threaded means.

It is an additional object of the present invention to provide a needle cover with a split cap that is unevenly split so that one of the uneven halves covers the tip of the needle when the needle is not in use and facilitates easy recovering of the needle including covering the tip after the needle has been used.

It is another object of the present invention to provide a simple and efficient way to expose the needle by having the unequal halves of the cover rotate away from each other, and then recover the needle by having the unequal halves rotate toward each other back to the close position, to thereby eliminate any possible motion of the exposed needle toward a user's finger when it is being recovered. In addition, the tip of the needle is covered by one unequal half so that the tip cannot possibly protrude through the split halves of the cover, even in the closed position.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a perspective view of the preferred embodiment of the present invention needle cover assembly connected to a syringe.

FIG. 2 is a perspective view of the needle cover assembly with the two halves in the open condition.

FIG. 3 is a perspective view of a hypodermic needle attached to a hub member and a protruding flange extending outwardly from the hub member.

FIG. 4 is an enlarged perspective view of the rotatable collar member with two recess notches.

FIG. 5 is an enlarged cross-sectional view taken along line 5—5 of FIG. 4.

FIG. 6 is a perspective view of an alternative embodiment of the present invention needle cover assembly connected to a syringe.

FIG. 7 is a top plan view of the alternative embodiment of the present invention needle cover assembly in the closed position.

FIG. 8 is a top plan view of the alternative embodiment of the present invention needle cover assembly in the open position.

FIG. 9 is an enlarged cross-sectional view taken along line 9—9 of FIG. 7.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIG. 1, there is shown a preferred embodiment of the present invention needle cover assembly 2 which is connected to a conventional syringe 4. The connection of the needle cover assembly 2 to the syringe 4 may be by any conventional means such as a pushfit or threadedly mounted.

Referring to FIGS. 1, 2 and 3, the needle cover assembly 2 includes a hollow hub member 8, a rotatable collar 20 and an elongated cover member 10 which encloses a hypodermic needle 6. The hypodermic needle 6 and the hollow hub member 8 include a proximal end and a distal end. The needle cover assembly 2 utilizes the conventional female connecting portion which is connectable to the male connecting portion on a conventional syringe 4. The proximal end of the hollow hub member 8 is connectable to a male portion of the conventional syringe 4. The distal end of the hollow hub member 8 is connected to the proximal end of the hypodermic needle 6.

The elongated cover member 10 is split longitudinally into two unequal halves 16, 18 which, in the closed position abut and parallel to each other. In the open position, as shown in FIG. 2, the two halves 16, 18 open to form a 90° opening for allowing the hypodermic needle 6 to inject the medicine to a patient. The two unequal halves 16, 18 are split asymmetrically. Each half of the cover member 10 comprises a proximal end and a distal end. The distal end of the first half 16 has an arc shaped portion which is complementary to the distal end of the second half 18 and forms a hollow chamber completely enclosing the hypodermic needle 6. By way of example, the first half 16 of the cover member 10 is actually a 270° portion of a cylindrical dome top member and the second half 18 is the complementary 90° portion of the cylindrical dome top member. When the two halves 16, 18 are closed, the two halves 16, 18 form the complete cylindrical dome top member. The proximal ends of the two halves 16, 18 are hingeably attached to the circumferential exterior sidewall 14 of the hollow hub member 8. The critical feature is that the large unequal half 16 has its distal end completely covering the needle 6 when in the closed position as shown in FIG. 1. In this way, a user cannot accidentally prick himself with the tip of the needle 6. It is emphasized that the selection of first half 16 being approximately a 270° arc cylinder and the second half 18 being approximately a 90° arc cylinder is one design choice. The key concept is that the larger unequal half 16 needs to have its dome portion cover the tip of the needle when in the closed position so a user cannot accidentally prick himself with the needle tip. In prior art needle covers, where the two halves are equal, there is a crack at the equal joinder location which is precisely where the tip of the needle is located and this allows someone to get pricked with the needle tip which is exactly at this location. The present invention eliminates this possibility.

A protruding flange 12 is integrally molded to the circumferential exterior sidewall 14 of the hollow hub member 8 and is located adjacent to the proximal end. The protruding flange 12 allows for pivotal movement of the two unequal halves 16, 18 from a full vertical position to a 90° angle opening.

Referring to FIGS. 2, 4 and 5, the rotatable collar 20 comprises a top rim 22, a bottom rim 24 and a circumferential sidewall 26. The circumferential sidewall 26 includes a first recess notch 28 and an opposite second recess notch 30 and are located at the top rim 22. These recess notches 28, 30 are utilized to allow the two halves 16, 18 of the cover member 10 to open for exposing the hypodermic needle 6. The circumferential sidewall 26 comprises an exterior surface and an interior surface with a locking groove 32 which is located adjacent to the bottom rim 24 of the rotatable collar 20. The locking groove 32 extends between the two recess notches 28, 30 which is about 90°, as illustrated in FIG. 5. When the rotatable collar 20 is assembled onto the hollow hub member 8, the locking groove 32 is tightly engaged with the protruding flange 12 of the hollow hub member 8. The interior sidewall of the rotatable member 20 conforms to the exterior sidewall 14 of the hollow hub member 8.

The hollow hub member 8, the elongated cover member 10 and the rotatable collar member 20 can be made by injection molding of plastic or any other suitable method.

In operation, when the rotatable collar 20 is rotated 90°, the two unequal halves 16, 18 of the elongated cover member 10 are allowed to open into the two recess notches 28, 30 on the top rim 22 of the rotatable collar member 20. When the rotatable collar 20 is rotated back, the two unequal halves 16, 18 are forced back together by the top rim 22 of the rotatable collar member 20 to cover the hypodermic needle 6.

The present invention has many advantages over prior art needle caps in that at no point during the closing or opening procedures does the doctor or nurse have to move their hand or fingers in the direction of the hypodermic needle point. As previously described, the hazard of someone's hand moving toward the needle point is eliminated. The opening and closing of the needle cap is by a simple rotation movement of the collar 20 and is a much safer procedure.

Referring to FIG. 6, there is shown a perspective view of an alternative embodiment of the present invention needle cover assembly 42 which can be connected to a conventional syringe, not shown. The connection of the needle cover assembly 42 to the syringe may be by any conventional means such as a pushfit or threadedly mounted.

There is a top plan view of the needle cover assembly 42 in the closed position shown in FIG. 7. The needle cover assembly 42 includes a hollow hub member 48, a rotatable collar member 60 and an elongated cover member 50 which encloses a hypodermic needle 46. The hypodermic needle 46 and the hollow hub member 48 include a proximal end and a distal end. The needle cover assembly 42 utilizes the conventional female connecting portion which is connectable to the male connecting portion on a conventional syringe. The proximal end of the hollow hub member 48 is connectable to a male portion of the conventional syringe. The distal end of the hollow hub member 48 is connected to the proximal end of the hypodermic needle 46.

The elongated cover member 50 is split longitudinally into two unequal halves 56, 58 which, in the closed position abut and are parallel to each other. In the open position shown in FIG. 8, the two halves 56, 58 open to form a 180° opening perpendicular to the hypodermic needle 46 for allowing the hypodermic needle 46 to inject the medicine into a patient. The two halves 56, 58 are split asymmetrically. Each half of the cover member 50 comprises a proximal end and a distal end. The distal end of the first half 56 has an arc shaped portion which is complementary to the distal end of the second half 58 and forms a hollow chamber completely enclosing the hypodermic needle 46. By way of example, the first half 56 of the cover member 50 is actually a 270° portion of a cylindrical dome top member and the second half 58 is the complementary 90° portion of the cylindrical dome top member. When the two halves 56, 58 are closed, the two halves 56, 58 form the complete cylindrical dome top member. The proximal ends of the two halves 56, 58 are hingeably attached to the circumferential exterior sidewall 54 of the hollow hub member 48. The two halves 56, 58 of the cover member 50 include two protruding flanges 52, 53 which are integrally molded to the exterior surface. As with the first embodiment, the central feature is that the larger unequal half 56 has its distal end completely covering the needle 46 when in the closed position as shown in FIG. 6. In this way, a user cannot accidentally prick himself with the tip of the needle 6. As with the first embodiment, it is emphasized that the selection of first half 56 being approximately a 270° arc cylinder and the second half 58 being approximately a 90° arc cylinder is one design choice. The key concept is that the larger unequal half 56 needs to have its dome portion cover the tip of the needle when in the closed position so a user cannot accidentally prick himself with the needle tip.

Referring to FIGS. 7, 8 and 9, the rotatable collar member 60 comprises a top rim 62, a bottom rim 64 and a circumferential sidewall 66. The circumferential sidewall 66 includes a first recess notch 68 and an opposite second recess notch 70 and are located at the top rim 62 of the rotatable collar member 60. These recess notches 68, 70 are utilized to allow the two halves 56, 58 of the cover member 50 to open for exposing the hypodermic needle 46. The circumferential sidewall 66 comprises an exterior and an interior surface with a locking groove 72.

Referring to FIGS. 7 and 8, the locking groove 72 extends all around the interior surface of the circumferential sidewall 66 and is located adjacent and parallel to the top rim 62. To open the two halves 56, 58 of the elongated cover member 50, the rotatable collar member 50 is rotated and the protruding flanges 52, 53 of the two halves 56, 58 engage with the locking groove 72. The protruding flanges 52, 53 travel along the locking groove 72 of rotatable collar 60. At points 98, the locking groove 72 will be facing inwardly towards the two halves 56, 58. At points 99, the locking groove 72 traverses and crosses over to the top rim 62. At points 100, the locking groove 72 will be facing upwardly. When the rotatable collar 60 is assembled onto the hollow hub member 48, the locking groove 72 is tightly engaged with the two protruding flange 52, 53 of the two halves 56, 58 of the cover member 50. The interior sidewall of the rotatable member 60 conforms to the exterior sidewall 54 of the hollow hub member 48.

The hollow hub member 48, the elongated cover member 50 and the rotatable collar member 60 can be made by injection molded plastic or other suitable method.

In operation, when the rotatable collar 60 is rotated 90°, the two halves 56, 58 of the elongated cover member 50 are allowed to open into the two recess notches 68, 70 by the two protruding flanges 52, 53 travelling along the locking groove 72. When the rotatable collar 60 is rotated back, the two halves 56, 58 are forced back together by the two recess notches 68, 70 and also by the two protruding flanges 52, 53 travelling along the locking groove 72.

Defined in detail, the present invention is a needle cover assembly, comprising: (a) a hypodermic needle having a proximal end and a distal end with a tip; (b) a hollow hub member having a proximal end, a distal end and a circumferential exterior sidewall, the proximal end connectable to a syringe, and the distal end connected to said proximal end of said hypodermic needle; (c) a protruding flange integrally molded to said circumferential exterior sidewall of said hollow hub member at a location adjacent to said proximal end; (d) an elongated cover member having a first half and an opposite unequal second half, each half having a proximal end and a distal end, the distal end of the first half being arc shaped, the distal end of the second half being complementary to the arc shaped distal end of the first half, to form a hollow chamber enclosing said hypodermic needle, the proximal ends of said halves hingeably attached to said exterior sidewall of said hollow hub member; (e) said first half of said elongated cover member having a greater arc than said unequal second half of said elongated cover member such that the distal end of said first half covers the tip of said hypodermic needle when in the closed position; and (f) a rotatable collar member having a top rim, a bottom rim and a circumferential sidewall with a first recess notch and an opposite second recess notch located at the top rim, the circumferential sidewall having an exterior surface and an interior surface with a locking groove located adjacent to the bottom rim for tightly engaging with said protruding flange of said hollow hub member, where the rotatable collar member is adapted securely to said circumferential exterior sidewall of said hollow hub member; (g) whereby when rotating said rotatable collar member, said unequal halves of said elongated cover member are allowed to open into said recess notches of said rotatable collar member to expose said hypodermic needle, and when said rotatable collar member rotate back, said unequal halves of said elongated cover member are forced back together to cover said hypodermic needle.

Defined broadly, the present invention is a needle cover assembly, comprising: (a) a needle including a tip connected to a hub, the hub having a proximal end, a distal end and an exterior sidewall with a protruding flange, where the proximal end connectable to a syringe; (b) a cover having a first half and an opposite unequal second half, each half having a proximal end and a distal end, the first half being complementary to the second half, to form a chamber enclosing said needle, the proximal ends of said halves hingeably attached to said exterior sidewall of said hub; (c) said first half of said cover having a greater arc than said unequal second half of said cover such that the distal end of said first half covers the tip of said needle when in the closed position; and (d) a collar having a top rim, a bottom rim and a sidewall with two recess notches opposite each other and located at the top rim, the sidewall having an interior surface with a groove for tightly engaging with said protruding flange of said hub; (e) whereby when rotating said collar, said halves of said cover are allowed to open into said two recess notches of said collar to expose said needle, and when said collar is rotated back, said halves of said cover are forced back together to cover said needle.

Defined alternatively in detail, the present invention is a needle cover assembly, comprising: (a) a hypodermic needle having a proximal end and a distal end with a tip; (b) a hollow hub member having a proximal end, a distal end and a circumferential exterior sidewall, the proximal end connectable to a syringe, and the distal end connected to said proximal end of said hypodermic needle; (c) an elongated cover member having a first half and an opposite unequal second half, each half having a proximal end, a distal end, an exterior surface and an interior surface, the distal end of the first half being arc shaped, the distal end of the second half being complementary to the arc shaped distal end of the first half, to form a hollow chamber enclosing said hypodermic needle, the proximal ends of said halves hingeably attached to said exterior sidewall of said hollow hub member; (d) said first half of said elongated cover member having a greater arc than said unequal second half of said elongated cover member such that the distal end of said first half covers the tip of said hypodermic needle when in the closed position; (e) a protruding flange extending outwardly from said exterior surfaces of said each half of said elongated cover member; and (f) a rotatable collar member having a top rim, a bottom rim and a circumferential sidewall with a first recess notch and an opposite second recess notch located at the top rim, the circumferential sidewall having an exterior surface and an interior surface with a locking groove extending all around the rotatable collar member and located adjacent and parallel to the top rim, the locking groove also extending into the first and second recess notches for tightly engaging with said protruding flanges of said elongated cover member, where the rotatable collar member is adapted securely to said circumferential exterior sidewall of said hollow hub member; (g) whereby when rotating said rotatable collar member, said unequal halves of said elongated cover member are allowed to open into said recess notches of said rotatable collar member opposite to each other and exposing said hypodermic needle, and when said rotatable collar member is rotated back, said unequal halves of said elongated cover member are forced back together to cover said hypodermic needle.

Defined alternatively broadly, the present invention is a needle cover assembly, comprising: (a) a needle including a tip connected to a hub, the hub having a proximal end, a distal end and an exterior sidewall, where the proximal end is connectable to a syringe; (b) a cover having a first half and an opposite unequal second half, each half having a proximal end, a distal end and an exterior surface with a protruding flange, the first half being complementary to the second half, to form a chamber enclosing said needle, the proximal ends of said halves hingeably attached to said exterior sidewall of said hub; (c) said first half of said cover having a greater arc than said unequal second half of said cover such that the distal end of said first half covers the tip of said needle when in the closed position; and (d) a collar having a top rim, a bottom rim and a sidewall with two recess notches located at the top rim opposite each other, the sidewall having an interior surface with a groove for tightly engaging with said protruding flanges of said cover, where the collar is adapted securely to said exterior sidewall of said hub; (e) whereby when rotating said collar, said halves of said cover are allowed to open into said recess notches of said collar opposite to each other and exposing said needle, and when said collar is rotated back, said halves of said cover are forced back together parallel to each other and covering said needle.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A needle cover assembly, comprising:
   a. a hypodermic needle having a proximal end and a distal end with a tip;
   b. a hollow hub member having a proximal end, a distal end and a circumferential exterior sidewall, the proximal end connectable to a syringe, and the distal end connected to said proximal end of said hypodermic needle;
   c. a protruding flange integrally molded to said circumferential exterior sidewall of said hollow hub member at a location adjacent to said proximal end;
   d. an elongated cover member having a first half and an opposite unequal second half, each half having a proximal end and a distal end, the distal end of the first half being arc shaped, the distal end of the second half being complementary to the arc shaped distal end of the first half, to form a hollow chamber enclosing said hypodermic needle, the proximal ends of said halves hingeably attached to said exterior sidewall of said hollow hub member;
   e. said first half of said elongated cover member having a greater arc than said unequal second half of said elongated cover member such that the distal end of said first half covers the tip of said hypodermic needle when in the closed position; and
   f. a rotatable collar member having a top rim, a bottom rim and a circumferential sidewall with a first recess notch and an opposite second recess notch located at the top rim, the circumferential sidewall having an exterior surface and an interior surface with a locking groove located adjacent to the bottom rim for tightly engaging with said protruding flange of said hollow hub member, where the rotatable collar member is adapted securely to said circumferential exterior sidewall of said hollow hub member;
   g. whereby when rotating said rotatable collar member, said unequal halves of said elongated cover member are allowed to open into said recess notches of said rotatable collar member to expose said hypodermic needle, and when said rotatable collar member is rotated back, said unequal halves of said elongated cover member are forced back together to cover said hypodermic needle.

2. The invention as defined in claim 1 wherein said hollow hub member, said elongated cover member and said rotatable collar member are made of injection molded plastic.

3. The invention as defined in claim 1 wherein said locking groove is between said first recess notch and said second recess notch which extends 90° on said interior surface of said rotatable collar member.

4. A needle cover assembly, comprising:
   a. a needle including a tip connected to a hub, the hub having a proximal end, a distal end and an exterior sidewall with a protruding flange, where the proximal end is connectable to a syringe;
   b. a cover having a first half and an opposite unequal second half, each half having a proximal end and a distal end, the first half being complementary to the second half, to form a chamber enclosing said needle, the proximal ends of said halves hingeably attached to said exterior sidewall of said hub;
   c. said first half of said cover having a greater arc than said unequal second half of said cover such that the distal end of said first half covers the tip of said needle when in the closed position; and
   d. a collar having a top rim, a bottom rim and a sidewall with two recess notches opposite each other and located at the top rim, the sidewall having an interior surface with a groove for tightly engaging with said protruding flange of said hub;
   e. whereby when rotating said collar, said halves of said cover are allowed to open into said two recess notches of said collar to expose said needle, and when said collar is rotated back, said halves of said cover are forced back together to cover said needle.

5. The invention as defined in claim 4 wherein said hub, said cover and said collar are made of injection molded plastic.

6. The invention as defined in claim 4 wherein said groove is between said two recess notches which extends 90° on said interior surface of said collar.

* * * * *